(12) United States Patent
Boylan

(10) Patent No.: US 11,946,466 B2
(45) Date of Patent: Apr. 2, 2024

(54) MEDICAL FLUID THERAPY MACHINE INCLUDING PNEUMATIC PUMP BOX AND ACCUMULATORS THEREFORE

(71) Applicants: Baxter International Inc., Deerfield, IL (US); Baxter Healthcare SA, Glattpark (CH)

(72) Inventor: Charles Wayne Boylan, St. Louis, MO (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 563 days.

(21) Appl. No.: 15/336,266

(22) Filed: Oct. 27, 2016

(65) Prior Publication Data

US 2018/0117233 A1    May 3, 2018

(51) Int. Cl.
*F15B 1/04*    (2006.01)
*A61M 1/26*    (2006.01)
(Continued)

(52) U.S. Cl.
CPC ............. *F04B 43/06* (2013.01); *A61M 1/267* (2014.02); *A61M 1/28* (2013.01); *A61M 1/3413* (2013.01);
(Continued)

(58) Field of Classification Search
CPC ...... F15B 1/04; F15B 1/16; F15B 2201/3155; F15B 2201/40; F15B 2201/4053; F15B 2201/4056; F15B 2201/405; F15B 2201/22; F04B 43/073; F04B 23/02; F04B 23/08; F04B 7/02; F04B 7/0266; F04B 7/0275; F04B 9/08; F04B 9/12; F04B 9/1207;
(Continued)

(56) References Cited

U.S. PATENT DOCUMENTS 1,392,861 A * 10/1921 Tabacco ................. A63H 27/10
446/186
3,847,182 A * 11/1974 Greer ........................ F15B 1/14
138/30
(Continued)

OTHER PUBLICATIONS

International Search Report and Written Opinion dated Feb. 2, 2018 issued in corresponding PCT Application No. PCT/US2017/058783.

*Primary Examiner* — Nathan C Zollinger
*Assistant Examiner* — Timothy P Solak
(74) *Attorney, Agent, or Firm* — K&L Gates LLP

(57) ABSTRACT

A medical fluid delivery machine including: a medical fluid pump including a pneumatically actuated pump chamber and first and second pneumatically actuated medical fluid valve chambers located respectively upstream and downstream of the pneumatically actuated pump chamber; a compressor for creating positive pressure air; and an accumulator storing the positive pressure air for delivery to at least one of the pneumatically actuated pump chamber, the first pneumatically actuated medical fluid valve chamber, or the second pneumatically actuated medical fluid valve chamber, the accumulator holding an elastic bladder that inflates under positive pressure air from the compressor, creating additional positive pressure that increases the amount of positive pressure air that the accumulator can provide.

16 Claims, 7 Drawing Sheets

(51) Int. Cl.
  A61M 1/28    (2006.01)
  A61M 1/34    (2006.01)
  A61M 39/22   (2006.01)
  F04B 23/02   (2006.01)
  F04B 23/08   (2006.01)
  F04B 43/06   (2006.01)
  F04B 53/06   (2006.01)
  F04B 7/02    (2006.01)
  F04B 9/12    (2006.01)
  F04B 9/123   (2006.01)
  F04B 9/127   (2006.01)
  F04B 39/10   (2006.01)
  F04B 41/02   (2006.01)
  F04B 43/073  (2006.01)
  F04B 53/10   (2006.01)

(52) U.S. Cl.
  CPC .............. A61M 39/22 (2013.01); F04B 23/02 (2013.01); F04B 23/08 (2013.01); F04B 53/06 (2013.01); F15B 1/04 (2013.01); A61M 2205/07 (2013.01); F04B 7/0275 (2013.01); F04B 9/12 (2013.01); F04B 9/123 (2013.01); F04B 9/1276 (2013.01); F04B 39/10 (2013.01); F04B 41/02 (2013.01); F04B 43/073 (2013.01); F04B 53/10 (2013.01); F15B 2201/3152 (2013.01); F15B 2201/3156 (2013.01); F15B 2201/40 (2013.01); F15B 2201/405 (2013.01)

(58) Field of Classification Search
  CPC ...... F04B 9/1215; F04B 9/1222; F04B 9/123; F04B 9/1256; F04B 9/1276; F04B 9/1315; F04B 17/06; F04B 41/02; F04B 43/0009; F04B 2205/063
  USPC ......................................................... 417/542
  See application file for complete search history.

(56)           References Cited
               U.S. PATENT DOCUMENTS

| 3,883,046 | A | * | 5/1975 | Thompson | B65D 88/62 |
| | | | | | 222/386.5 |
| 3,940,026 | A | * | 2/1976 | Kain | B65D 83/0061 |
| | | | | | 222/215 |
| 3,993,069 | A | * | 11/1976 | Buckles | A61J 1/05 |
| | | | | | 222/215 |
| 4,136,696 | A | * | 1/1979 | Nehring | A61M 3/0216 |
| | | | | | 604/142 |
| 4,222,499 | A | * | 9/1980 | Lee | B65D 83/0061 |
| | | | | | 222/215 |
| 4,548,550 | A | * | 10/1985 | Tsuji | A61M 1/1086 |
| | | | | | 417/390 |
| 4,832,005 | A | * | 5/1989 | Takamiya | A61M 1/1062 |
| | | | | | 600/18 |
| 5,031,510 | A | * | 7/1991 | Krauter | B25J 9/104 |
| | | | | | 403/316 |
| 5,549,139 | A | * | 8/1996 | Perkins | A61M 1/72 |
| | | | | | 137/884 |
| 5,628,908 | A | | 5/1997 | Kamen et al. | |
| 6,416,293 | B1 | * | 7/2002 | Bouchard | A61M 1/362265 |
| | | | | | 417/313 |
| 8,029,454 | B2 | | 10/2011 | Kelly et al. | |
| 8,393,690 | B2 | * | 3/2013 | Grant | A61M 1/16 |
| | | | | | 312/209 |
| 8,826,940 | B2 | * | 9/2014 | Barth | F15B 1/04 |
| | | | | | 303/DIG. 11 |
| 2009/0152379 | A1 | * | 6/2009 | Harter | B05B 9/0838 |
| | | | | | 239/373 |
| 2011/0079140 | A1 | * | 4/2011 | Baseley | F15B 1/26 |
| | | | | | 92/90 |
| 2011/0197971 | A1 | * | 8/2011 | Gaignet | C02F 1/288 |
| | | | | | 137/1 |
| 2011/0214424 | A1 | * | 9/2011 | Wood | E21F 17/00 |
| | | | | | 60/639 |
| 2012/0085449 | A1 | * | 4/2012 | Barth | F15B 1/04 |
| | | | | | 138/30 |
| 2012/0192979 | A1 | * | 8/2012 | Barth | F15B 1/04 |
| | | | | | 138/30 |
| 2014/0228758 | A1 | * | 8/2014 | Chi | A61M 5/148 |
| | | | | | 604/132 |
| 2014/0276376 | A1 | | 9/2014 | Rohde et al. | |
| 2015/0338012 | A1 | * | 11/2015 | Cogliati | B32B 27/08 |
| | | | | | 138/30 |
| 2017/0097121 | A1 | * | 4/2017 | Johnson | F17C 13/025 |
| 2017/0165435 | A1 | * | 6/2017 | Green | A61M 5/14 |

* cited by examiner

MEDICAL FLUID THERAPY MACHINE INCLUDING PNEUMATIC PUMP BOX AND ACCUMULATORS THEREFORE

BACKGROUND

The present disclosure relates generally to devices, systems and methods for medical fluid delivery machines. More specifically, the present disclosure relates to medical fluid delivery machines, such as renal failure therapy machines, that employ pneumatic pumping.

Regarding renal failure therapy machines, due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that frequent treatments remove more toxins and waste products than a patient receiving less frequent, but perhaps longer treatments. A patient receiving more frequent treatments does not experience as much of a down cycle as does an in-center patient, who has built-up two or three days' worth of toxins prior to a treatment. In certain areas, the closest dialysis center can be many miles from the patients' home causing door-to-door treatment time to consume a large portion of the day. HHD may take place overnight or during the day while the patient relaxes, works or is otherwise productive.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

Any of the above modalities performed by a machine may employ pneumatic pumping. Pneumatic pumping typically involves the application of positive and/or negative air pressure to a pumping membrane or diaphragm. Positive pressure may be provided via a compressor feeding a positive pressure tank or accumulator. Negative pressure may be provided via a vacuum pump feeding a negative pressure tank or accumulator. Attempts may be made to remove water from the positive pressure prior to the air being fed to the positive pressure tank accumulator. Water present in positive pressure air can lead to corrosion within the solenoid valves and elsewhere.

The components described above may generate heat or may operate more effectively in a non-heated environment. An improved coordination of such components is needed accordingly.

Additionally, the positive pressure accumulator is effective only until its pressure reaches that needed to drive a certain application. For example, a pressure regulator may be present between the positive pressure accumulator and the application, e.g., a fluid valve. If the regulator is set to deliver 5 psig to close the valve, for example, then the accumulator cannot deliver the pressure necessary to close the valve once its pressure falls below 5 psig. There may be situations in which it is desirable to have the positive and negative accumulators deliver positive and negative pressure, respectively, for as long as possible. An additional need exists accordingly to extend the useful life of the pneumatic pressure accumulators.

SUMMARY

The examples described herein disclose pump box devices, systems and methods therefore applicable, for example, to fluid delivery for: plasmapheresis, hemodialysis ("HD"), hemofiltration ("HF") hemodiafiltration ("HDF"), and continuous renal replacement therapy ("CRRT") treatments. The pump box devices, and systems and methods therefore described herein are also applicable to peritoneal dialysis ("PD") and to intravenous drug delivery. These modalities may be referred to collectively or generally individually as medical fluid delivery.

Moreover, each of the devices, systems and methods described herein may be used with clinical or home-based machines. For example, the systems may be employed in in-center HD, HF or HDF machines, which run throughout the day. Alternatively, the systems may be used with home HD, HF or HDF machines, which are operated at the patient's convenience. One such home system is described in U.S. Pat. No. 8,029,454 ("the '454 patent"), issued Oct. 4, 2011, entitled "High Convection Home Hemodialysis/Hemofiltration And Sorbent System", filed Nov. 4, 2004, assigned to the assignee of the present application. Another such home system is described in U.S. Pat. No. 8,393,690 ("the '690 patent"), issued Mar. 12, 2013, entitled "Enclosure for a Portable Hemodialysis System", filed Aug. 27, 2008. The entire contents of each of the above references are incorporated herein by reference and relied upon.

In an embodiment, a medical fluid delivery machine is provided that includes a medical fluid delivery chassis. The medical fluid delivery chassis houses components needed to deliver medical fluid, such as one or more pump, plural valves, a heater if needed, online medical fluid generation equipment if needed and desired, plural sensors, such as any one, or more, or all of pressure sensors, conductivity sensors, temperature sensors, air detectors, blood leak detectors, and the like, a user interface, and a control unit, which may employ one or more processor and memory to control the above-described equipment.

Various components, such as the fluid pumps and valves, may be actuated pneumatically. In such a case, it is contemplated to provide a pneumatic pump box, which houses equipment needed to generate and store positive and/or negative pressure air. "Air" as used herein means air as it exists naturally, which is made up of individual gases such as nitrogen, oxygen, argon, and carbon dioxide. "Air" may also include a desired modified atmosphere, such as a larger percentage of, or a pure gas, such nitrogen or carbon dioxide. The term "pneumatic" also refers to naturally occurring air and/or any type of modified atmosphere.

The pneumatic pump box may house components, such as a vacuum pump for supplying negative air pressure, a compressor for supplying positive air pressure, a dryer for removing water from the positive pressure air outputted from the compressor prior to storage in the accumulator, and positive and negative accumulators for storing positive and negative air pressure, respectively. The pneumatic pump box may be attached removeably to the medical fluid delivery chassis. If the medical fluid delivery machine is to be operated while the patient is sleeping, for example, or if the patient desires a quiet environment for whatever reason, it may be desirable for the patient to remove the pneumatic pump box and store it in a closet or other remote location to dampen its noise. The removable pneumatic pump box is connected pneumatically to the medical fluid delivery chassis via one or more positive and negative pressure lines and may receive electrical power via its own electrical cord or via an electrical power feed from the chassis.

The pneumatic pump box's vacuum pump is typically the hottest point in the box during operation. The dryer in an embodiment cools air from the compressor to condense water from the compressed air, so that the water may be removed before being delivered into the positive pressure accumulator. Removing water from the compressed air is important because water in the compressed air volume may cause system failure due to corrosion. The pneumatic box of the present disclosure accordingly places the vacuum pump at the top of the pneumatic pump box. Here, heat rises from the vacuum pump to the top of the box, such that its impact on the other components in the box is minimized. It is further contemplated to place a small, inexpensive fan directly in the top of the box directly above the dryer, which is oriented to pull the heated air out of the box. Intake vents for the fan may be provided in the pump box, e.g., just below the vacuum pump.

With the vacuum pump placed at the top of the pump box, the goals for locating the remainder of the equipment are two-fold, namely, (i) to locate the dryer as far away from the vacuum pump as possible to prevent heat generated from the vacuum pump from heating the dryer, and (ii) to reduce and simplify the routing of tubing between the pneumatic pump box as much as possible. To this end, either the compressor or the dryer may be located at the bottom of the box. Locating the compressor at the bottom of the box, the dryer above the compressor and the accumulators above the dryer optimizes the routing of tubing and other air connections, which run from the compressor to the dryer, and from the dryer to the positive pressure accumulator. On the other hand, locating the dryer at the bottom of the box, the compressor above the dryer, and the accumulators above the compressor, spaces the dryer (e.g., chilling device) as far away as possible from the heat-producing vacuum pump.

In an embodiment, the pneumatic pump box includes two accumulators, namely, a positive pressure accumulator and a negative pressure accumulator. It is possible that the pneumatic pump and valve control may use different pressure levels at different locations within the medical fluid delivery machine. For example, a pneumatic pump may include a pump chamber associated with its own inlet and outlet valve chambers, wherein the pressure applied to the valve chambers is greater than the pressure applied to the pump chamber, so that operation of the pump chamber does not affect a desired valve state. In another example, it may be desirable to apply less pressure to a blood pump operation than to a dialysis fluid operation, to better avoid damaging blood cells or other blood components. In any case, multiple accumulators may be provided to store multiple positive and/or negative pressures. In one preferred embodiment, however, a single positive pressure accumulator and a single negative pressure accumulator are provided to feed multiple pneumatic regulators that set the different desired positive and/or negative pneumatic operating pressures.

The pneumatic regulators may include static regulators that set a desired positive or negative pneumatic pressure, for example, to feed multiple on/off or binary applications. The pneumatic regulators may alternatively or additionally include a variable diameter orifice, e.g., as a variable valve or vari-valve. Components, such as the pneumatic regulators, binary pneumatic valves and the vari-valves are placed in an embodiment on a manifold that is located inside the medical fluid delivery chassis, so that single positive and negative pressure lines from the pneumatic pump box to the chassis can feed each of the components of the manifold.

To improve the efficiency of the accumulators, it is contemplated to sealingly secure an elastic accumulator bladder inside of an outer, rigid positive pressure accumulator housing, which limits the size to which the bladder can expand, and also defines the shape of the bladder when expanded to fill the volume of the accumulator housing fully. The bladder is formed to require a certain positive pressure for inflation, namely, the bladder inflation pressure. The rigid outer chamber is vented in an embodiment, so that air between the bladder and rigid outer chamber can be displaced to atmosphere when the bladder is inflated. When positive pressure air is withdrawn initially from the accumulator bladder, no shape change occurs, and the accumulator assembly acts as a conventional ridged accumulator until the pressure in the bladder falls to the bladder inflation pressure. When the positive pressure starts to fall below the bladder inflation pressure, the accumulator bladder contracts and continues to deliver positive pressure air volume at the bladder inflation pressure until the accumulator bladder is fully contracted. During contraction, atmospheric air is drawn into the rigid outer container outside of the bladder via the vent. The overall volume of air delivered is greater than that possible with a rigid accumulator alone due to the force applied by the bladder elastomer to the internal bladder air volume.

Typically, the accumulator is charged via a compressor to a set pressure, which is above a desired operating pressure. The desired operating pressure is achieved by using a regulator to set an accurate downstream pneumatic pressure. It is contemplated to construct the bladder to make the bladder inflation pressure just slightly above the desired operating pressure. In this manner, most all of the pressure delta between the set charging pressure and the desired operation pressure is consumed prior to the contraction of the bladder.

In an embodiment, the fluid valves are closed under positive pressure and opened by venting the positive pressure to atmosphere. For example, a first electrically operated solenoid valve may be provided to allow or not allow positive pressure to flow or not flow to the fluid valve. A second electrically operated solenoid valve is provided to allow or not allow the positive pressure to vent to atmosphere. To close the fluid valve, the first electrically operated solenoid valve is opened, while the second electrically operated solenoid valve is closed, which allows the fluid valve to see positive air pressure, which is not vented. To open the fluid valve, the first electrically operated solenoid valve is closed, while the second electrically operated solenoid valve is opened, which shuts off positive pressure to the fluid valve and vents the existing positive pressure at the fluid valve to atmosphere, enabling the fluid valve to open. The fluid valve may open due to the force of fluid pressure on the fluid side of a valve diaphragm and/or the valve diaphragm may be preformed or predomed and be placed or positioned so as to be biased fluid open when not under positive pressure. It should be appreciated then that in one embodiment, while the pump chamber requires positive and negative pneumatic pressure, the corresponding valve chambers only require positive pneumatic pressure. The life of the fluid pump including inlet and outlet valves may therefore be extended by extending the life of the positive pressure via the accumulator bladder of the present disclosure without a corresponding extension of the life of the negative pressure source.

Nevertheless, it is also contemplated to increase the life of the negative pressure source. Here, a reverse accumulator structure is applied to the negative pressure accumulator. In one example, an elastic bladder is preformed to have the same shape as for the positive pressure accumulator. The difference is that the vacuum is applied to the vent port of the positive chamber to draw a vacuum on the air between the bladder and the rigid outer chamber of the negative pressure accumulator. The vent port for the negative pressure accumulator is the port leading to the inside of the bladder (which is the supply port for the positive accumulator). The negative pressure bladder is thickened as necessary to fully inflate under a more negative pressure than the desired regulated negative pressure, so that the bladder can provide the negative pressure to drive the negative regulator until the bladder is fully contracted. In various embodiments, (i) the bladder and the ridged outer housing accumulator are configured so that a full vacuum can be drawn before the negative pressure bladder expands to block or fully block the vacuum port provided by the housing, and/or (ii) the vacuum port can be angled on the inside of the rigid housing so that it is difficult for the bladder to block. Thus unlike the positive pressure bladder, which does not contract until positive pressure inside the bladder falls to the bladder inflation pressure, the negative pressure accumulator begins to contract after the negative pressure in the vacuum line starts to become less negative than the required negative bladder inflation pressure (not enough negative pressure to keep the bladder fully expanded. However, the negative pressure remains at the negative pressure inflation pressure until the bladder is fully contracted, leaving the rigid outer chamber virtually fully charged with negative pressure to drive the negative regulator.

As discussed herein, in both the positive and negative pressure bladder instances, the outer, rigid accumulator housing is vented to atmosphere so that the bladder can inflate and contract freely under positive or negative pressure.

It may be desirable that to still be able to deliver positive and/or negative air pressure when power to the medical fluid delivery machine is lost. For example, it may be desirable to push blood back to the patient to allow the patient to disconnect from a dialysis machine. Here, the dialysis machine may provide battery power to power the pneumatic valves, enabling pneumatic pressure to be applied to the fluid valves and pump chambers. The bladders increase the volume of positive and negative pressure air that can be extracted from the accumulators to maintain the desired working pressure for a longer period, allowing more blood to be pushed back to the patient. Alternatively or additionally, the additional working pressure may be used to lower the leak tightness requirements of the on-off binary and vari-valves, making the overall machine more robust.

In light of the disclosure herein and without limiting the disclosure in any way, in a first aspect of the present disclosure, which may be combined with any other aspect listed herein unless specified otherwise, a medical fluid delivery machine includes: a medical fluid pump including a pneumatically actuated pump chamber and first and second pneumatically actuated medical fluid valve chambers located respectively upstream and downstream of the pneumatically actuated pump chamber; a compressor for creating positive pressure air; and an accumulator storing the positive pressure air for delivery to at least one of the pneumatically actuated pump chamber, the first pneumatically actuated medical fluid valve chamber, or the second pneumatically actuated medical fluid valve chamber, the accumulator holding an elastic bladder that inflates under positive pressure air from the compressor, creating additional positive pressure that increases the amount of positive pressure air that the accumulator can provide.

In a second aspect of the present disclosure, which may be combined with any other aspect listed herein unless specified otherwise, the accumulator includes an outer rigid housing holding the elastic bladder, and wherein the bladder is held in a sealed relationship with the outer rigid housing.

In a third aspect of the present disclosure, which may be combined with the second aspect in combination with any other aspect listed herein unless specified otherwise, the outer rigid housing is vented.

In a fourth aspect of the present disclosure, which may be combined with the second aspect in combination with any other aspect listed herein unless specified otherwise, the medical fluid delivery machine includes a connector forming the sealed relationship between the bladder and the outer rigid housing.

In a fifth aspect of the present disclosure, which may be combined with the fourth aspect in combination with any other aspect listed herein unless specified otherwise, the connector includes a sealing end configured to seal to the open end of the bladder and a tube connecting end configured to seal to a pneumatic tube extending from the accumulator.

In a sixth aspect of the present disclosure, which may be combined with the second aspect in combination with any other aspect listed herein unless specified otherwise, the outer rigid housing is countoured to enable the elastic bladder when expanded to conform at least substantially completely to an inner shape of the outer rigid housing.

In a seventh aspect of the present disclosure, which may be combined with the sixth aspect in combination with any other aspect listed herein unless specified otherwise, the bladder initially has a thin tube shape and expands to conform at least substantially completely to the inner shape of the outer rigid housing.

In an eighth aspect of the present disclosure, which may be combined with any other aspect listed herein unless specified otherwise, the medical fluid delivery machine includes a pneumatic regulator located between the accumulator and the at least one of the pneumatically actuated pump chamber, the first pneumatically actuated medical fluid valve chamber, or the second pneumatically actuated medical fluid valve chamber, the pneumatic regulator setting a desired output pressure for the positive pressure air, the bladder enabling the additional amount of the positive pressure air to be provided to the pneumatic regulator.

In a ninth aspect of the present disclosure, which may be combined with the eighth aspect in combination with any other aspect listed herein unless specified otherwise, the bladder is structured so that a pressure needed to inflate the bladder is slightly greater than the desired output pressure.

In a tenth aspect of the present disclosure, which may be combined with any other aspect listed herein unless specified otherwise, at least one of the first and second pneumatically actuated medical fluid valve chambers is closed via positive pressure and opened via venting to atmosphere.

In an eleventh aspect of the present disclosure, which may be combined with any other aspect listed herein unless specified otherwise, a medical fluid delivery machine includes: a medical fluid pump including a pneumatically actuated pump chamber and first and second pneumatically actuated medical fluid valve chambers located respectively upstream and downstream of the pneumatically actuated pump chamber; a vacuum pump for creating negative pressure; and an accumulator storing the negative pressure for operation with at least one of the pneumatically actuated pump chamber, the first pneumatically actuated medical fluid valve chamber or the second pneumatically actuated medical fluid valve chamber, the accumulator holding an elastic bladder that inflates under negative pressure from the vacuum pump applied to an outside of the elastic bladder, creating additional negative pressure that increases the amount of negative pressure that the accumulator can provide.

In a twelfth aspect of the present disclosure, which may be combined with the eleventh aspect in combination with any other aspect listed herein unless specified otherwise, the accumulator includes an outer rigid housing holding the elastic bladder, and wherein the bladder is held in a sealed relationship with the outer rigid housing.

In a thirteenth aspect of the present disclosure, which may be combined with the twelfth aspect in combination with any other aspect listed herein unless specified otherwise, negative pressure from the vacuum pump is applied to the accumulator via a port provided on the outer rigid housing located outside of the elastic bladder.

In a fourteenth aspect of the present disclosure, which may be combined with the thirteenth aspect in combination with any other aspect listed herein unless specified otherwise, at least one of (i) the outer rigid housing is countoured to enable the elastic bladder to fully inflate prior to blocking the port of the outer rigid housing or (ii) the outer rigid housing is countoured to enable the elastic bladder when inflated to conform at least substantially completely to an inner shape of the outer rigid housing.

In a fifteenth aspect of the present disclosure, which may be combined with the eleventh aspect in combination with any other aspect listed herein unless specified otherwise, the medical fluid delivery machine includes a pneumatic regulator located between the accumulator and the at least one of the pneumatically actuated pump chamber, the first pneumatically actuated medical fluid valve chamber, or the second pneumatically actuated medical fluid valve chamber, the pneumatic regulator setting a desired negative operating pressure, the bladder increasing the amount of negative pressure greater than the desired negative operating pressure for supply to the regulator.

In a sixteenth aspect of the present disclosure, which may be combined with the eleventh aspect in combination with any other aspect listed herein unless specified otherwise, the inside of the bladder is vented to atmosphere.

In a seventeenth aspect of the present disclosure, which may be combined with the eleventh aspect in combination with any other aspect listed herein unless specified otherwise, the bladder is preformed to have a thin tube shape that is thickened so that the bladder is configured to inflate at a negative pressure at least approximately equal to a desired negative pressure for the accumulator when fully charged.

In an eighteenth aspect of the present disclosure, which may be combined with any other aspect listed herein unless specified otherwise, a medical fluid delivery machine includes: a compressor for creating positive pressure air; a vacuum pump for creating negative pressure; a first accumulator storing the positive pressure air for delivery within the medical fluid machine, the first accumulator holding a first elastic bladder that inflates under positive pressure air from the compressor applied to an inside of the bladder, increasing the amount of positive pressure air that the accumulator can provide; and a second accumulator storing the negative pressure for operation within the medical fluid machine, the second accumulator holding a second elastic bladder that inflates under negative pressure from the vacuum pump applied to an outside of the bladder, increasing the amount of negative pressure that the accumulator can provide.

In a nineteenth aspect of the present disclosure, which may be combined with the eighteenth aspect in combination with any other aspect listed herein unless specified otherwise, the medical fluid delivery machine includes a pneumatically actuated pump chamber operated via the positive and negative pressure.

In a twentieth aspect of the present disclosure, which may be combined with the eighteenth aspect in combination with any other aspect listed herein unless specified otherwise, the first accumulator includes a first outer rigid housing holding the first elastic bladder and the second accumulator includes a second outer rigid housing holding the second elastic bladder.

In a twenty-first aspect of the present disclosure, which may be combined with any other aspect listed herein unless specified otherwise, a medical fluid delivery machine includes: a medical fluid pump including a pneumatically actuated pump chamber and first and second pneumatically actuated medical fluid valve chambers located respectively upstream and downstream of the pneumatically actuated pump chamber; and a location of the machine including a vacuum pump supplying negative pneumatic pressure for the medical fluid pump; an accumulator storing positive pressure air for the medical fluid pump, the accumulator located beneath the vacuum pump; a compressor for creating the positive pressure air, the compressor located beneath the accumulator; and a dryer for removing water from the positive pressure air outputted from the compressor prior to storage in the accumulator, the dryer located beneath the accumulator.

In a twenty-second aspect of the present disclosure, which may be combined with the twenty-first aspect in combination with any other aspect listed herein unless specified otherwise, the dryer is located between the accumulator and the compressor.

In a twenty-third aspect of the present disclosure, which may be combined with the twenty-first aspect in combination with any other aspect listed herein unless specified otherwise, the dryer is configured to cool the positive pressure air to remove water.

In a twenty-fourth aspect of the present disclosure, which may be combined with the twenty-first aspect in combination with any other aspect listed herein unless specified otherwise, the vacuum pump creates heat and is accordingly placed uppermost within the location of the machine.

In a twenty-fifth aspect of the present disclosure, which may be combined with the twenty-first aspect in combination with any other aspect listed herein unless specified otherwise, the location of the machine is a pneumatic pump box.

In a twenty-sixth aspect of the present disclosure, which may be combined with the twenty-fifth aspect in combination with any other aspect listed herein unless specified otherwise, the medical fluid delivery machine includes a medical fluid delivery chassis operating the medical fluid pump and the first and second medical fluid valve chambers, and wherein the pneumatic pump box is connected removeably to the medical fluid delivery chassis.

In a twenty-seventh aspect of the present disclosure, which may be combined with the twenty-fifth aspect in combination with any other aspect listed herein unless specified otherwise, the pneumatic pump box includes a fan venting heated air out of the pump box, the fan located above the dryer.

In a twenty-eighth aspect of the present disclosure, which may be combined with the twenty-fifth aspect in combination with any other aspect listed herein unless specified otherwise, the pneumatic pump box is insulated to dampen sound produced within the pump box.

In a twenty-ninth aspect of the present disclosure, which may be combined with the twenty-first aspect in combination with any other aspect listed herein unless specified otherwise, the accumulator is a first accumulator, and which includes a second accumulator storing negative pressure air via the vacuum pump, the second accumulator located beneath the vacuum pump.

In a thirtieth aspect of the present disclosure, which may be combined with the twenty-ninth aspect in combination with any other aspect listed herein unless specified otherwise, the compressor and the dryer are located beneath the first and second accumulators.

In a thirty-first aspect of the present disclosure, which may be combined with the twenty-first aspect in combination with any other aspect listed herein unless specified otherwise, the medical fluid delivery machine includes plural electrically actuated solenoid valves positioned and arranged to enable at least one of the negative pressure or positive pressure air from the location to reach the medical fluid pump.

In a thirty-second aspect of the present disclosure, which may be combined with any other aspect listed herein unless specified otherwise, any of the structure, functionality and alternatives illustrated and described in connection with any of FIGS. 1 to 8 may be combined with any of the structure, functionality and alternatives illustrated and described in connection with any other of FIGS. 1 to 9.

In light of the present disclosure and the above aspects, it is therefore an advantage of the present disclosure to provide an improved medical fluid delivery device.

It is another advantage of the present disclosure to provide an improved pneumatic pump box for a medical fluid delivery device.

It is a further advantage of the present disclosure to provide a pneumatic pump box for a medical fluid delivery device that is thermally efficient.

It is still another advantage of the present disclosure to provide a pneumatic pump box for a medical fluid delivery device having efficient tubing routing.

It is still a further advantage of the present disclosure to provide a pneumatic pressure accumulator having extended usability.

It is yet another advantage of the present disclosure to provide a pneumatic pumping system that can operate efficiently upon loss of power.

It is yet a further advantage of the present disclosure to provide a pneumatic pumping system that can preserve positive and negative pneumatic pressure.

The advantages discussed herein may be found in one, or some, but perhaps not all of the embodiments disclosed herein. Additional features and advantages are described herein, and will be apparent from, the following Detailed Description and the figures.

DETAILED DESCRIPTION

System Hardware

The examples described herein are applicable to any medical fluid delivery system that delivers a medical fluid, such as blood, dialysis fluid, substitution fluid or and intravenous drug ("IV"). The examples are particularly well suited for kidney failure therapies, such as all forms of hemodialysis ("HD"), hemofiltration ("HF"), hemodiafiltration ("HDF"), continuous renal replacement therapies ("CRRT") and peritoneal dialysis ("PD"), referred to herein collectively or generally individually as renal failure therapy. Moreover, the machines and any of the pneumatic pumping systems and methods described herein may be used in clinical or home settings. For example, a machine including pneumatic pumping structure may be employed in an in-center HD machine, which runs virtually continuously throughout the day. Alternatively, the pneumatic pumping structure may be used in a home HD machine, which can for example be run at night while the patient is sleeping. Moreover, each of the renal failure therapy examples described herein may employ a diffusion membrane or filter, such as a dialyzer, e.g., for HD or HDF, or a hemofilter, e.g., for HF.

Figure 1:
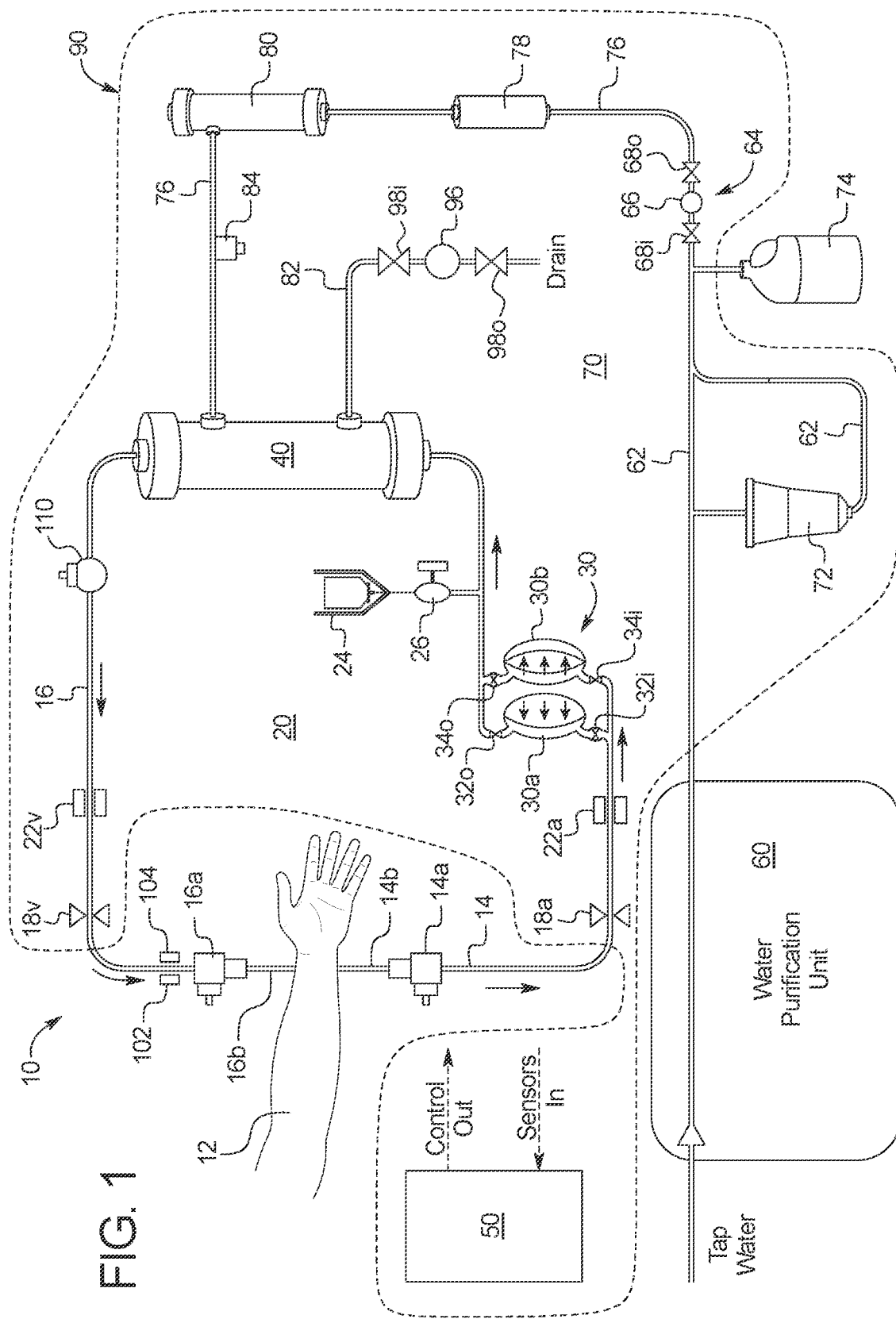
FIG. 1 is a schematic illustration of one embodiment of a renal failure therapy operated by a machine employing a pneumatic pump box including the pressure accumulators of the present disclosure.

Referring now to FIG. 1, an example of an HD flow schematic for a medical fluid delivery system 10 employing a pneumatic pump box of the present disclosure is illustrated. Because the HD system of FIG. 1 is relatively complicated, FIG. 1 and its discussion also provide support for any of the renal failure therapy modalities discussed above and for an IV machine. Generally, system 10 is shown having a very simplified version of a dialysis fluid or process fluid delivery circuit. The blood circuit is also simplified but not to the degree that the dialysis fluid circuit is simplified. It should be appreciated that the circuits have been simplified to make the description of the present disclosure easier, and that the systems if implemented would have additional structure and functionality, such as is found in the publications incorporated by reference above.

System 10 of FIG. 1 includes a blood circuit 20. Blood circuit 20 pulls blood from and returns blood to a patient 12. Blood is pulled from patient 12 via an arterial line 14, and is returned to the patient via a venous line 16. Arterial line 14 includes an arterial line connector 14a that connects to an arterial needle 14b, which is in blood draw communication with patient 12. Venous line 16 includes a venous line connector 16a that connects to a venous needle 16b, which is in blood return flow communication with the patient. Arterial and venous lines 14 and 16 also include line clamps 18a and 18v, which can be spring-loaded, fail-safe mechanical pinch clamps. Line clamps 18a and 18v are closed automatically in an emergency situation in one embodiment.

Arterial and venous lines 14 and 16 also include air or bubble detectors 22a and 22v, respectively, which can be ultrasonic air detectors. Air or bubble detectors 22a and 22v look for air in the arterial and venous lines 14 and 16, respectively. If air is detected by one of air detectors 22a and 22v, system 10 closes line clamps 18a and 18v, pauses the blood and dialysis fluid pumps, and provides instructions to the patient to clear the air so that treatment can resume.

A blood pump 30 is located in arterial line 14 in the illustrated embodiment. In the illustrated embodiment, blood pump 30 includes a first blood pump pod 30a and a second blood pump pod 30b. Blood pump pod 30a operates with an inlet valve 32i and an outlet valve 32o. Blood pump pod 30b operates with an inlet valve 34i and an outlet valve 34o. In an embodiment, blood pump pods 30a and 30b are each blood receptacles that include a hard outer shell, e.g., spherical, with a flexible diaphragm located within the shell, forming a diaphragm pump. One side of each diaphragm receives blood, while the other side of each diaphragm is operated by negative and positive air pressure. Blood pump 30 is alternatively a peristaltic pump operating with the arterial line 14 tube.

A heparin vial 24 and heparin pump 26 are located between blood pump 30 and blood filter 40 (e.g., dialyzer) in the illustrated embodiment. Heparin pump 26 may be a pneumatic pump or a syringe pump (e.g., stepper motor driven syringe pump). Supplying heparin upstream of blood filter 40 helps to prevent clotting of the filter's membranes.

A control unit 50 includes one or more processor and memory. Control unit 50 receives air detection signals from air detectors 22a and 22v (and other sensors of system 10, such as temperature sensors, blood leak detectors, conductivity sensors, pressure sensors, and access disconnection transducers 102, 104), and controls components such as line clamps 18a and 18v, blood pump 30, heparin pump 26, and the dialysis fluid pumps. Blood exiting blood filter 40 via venous line 16 flows through an airtrap 110. Airtrap 110 removes air from the blood before the dialyzed blood is returned to patient 12 via venous line 16.

With the hemodialysis version of system 10 of FIG. 1, dialysis fluid or dialysate is pumped along the outside of the membranes of blood filter 40, while blood is pumped through the insides of the blood filter membranes. Dialysis fluid or dialysate is prepared beginning with the purification of water via a water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structures to purify tap water (e.g., remove pathogens and ions such as chlorine), so that the water is in one implementation below 0.03 endotoxin units/ml ("EU/ml") and below 0.1 colony forming units/ml ("CFU/ml"). Water purification unit 60 may be provided in a housing separate from the housing of the hemodialysis machine, which includes blood circuit 20 and a dialysis fluid circuit 70.

Dialysis fluid circuit 70 is again highly simplified in FIG. 1 to ease illustration. Dialysis fluid circuit 70 in actuality may include all of the relevant structure and functionality set forth in the publications incorporated by reference above. Certain features of dialysis fluid circuit 70 are illustrated in FIG. 1. In the illustrated embodiment, dialysis fluid circuit 70 includes a to-blood filter dialysis fluid pump 64. Pump 64 is in one embodiment configured the same as blood pump 30. Pump 64, like pump 30, includes a pair of pump pods, which again may be spherically configured. The two pump pods, like with blood pump 30, are operated alternatingly so that one pump pod is filling with HD dialysis fluid, while the other pump pod is expelling HD dialysis fluid.

Pump 64 is a to-blood filter dialysis fluid pump. There is another dual pod pump chamber 96 operating with inlet valve 98i and outlet valve 98o located in drain line 82 to push used dialysis fluid to drain. There is a third pod pump (not illustrated) for pumping pump purified water through a bicarbonate cartridge 72. There is a fourth pod pump (not illustrated) used to pump acid from acid container 74 into mixing line 62. The third and fourth pumps, the concentrate pumps, may be single pod pumps because continuous pumping is not as important in mixing line 62 because there is a buffering dialysis fluid tank (not illustrated) between mixing line 62 and to-blood filter dialysis fluid pump 64 in one embodiment.

A fifth pod pump (not illustrated) provided in drain line 82 is used to remove a known amount of ultrafiltration ("UF") when an HD therapy is provided. System 10 keeps track of the UF pump to control and know how much ultrafiltrate has been removed from the patient. System 10 ensures that the necessary amount of ultrafiltrate is removed from the patient by the end of treatment.

Each of the above-described pumps may alternatively be a peristaltic pump operating with a tube. If so, the system valves may still be actuated pneumatically according to the features of the present disclosure.

In one embodiment, purified water from water purification unit 60 is pumped along mixing line 62 though bicarbonate cartridge 72. Acid from container 74 is pumped along mixing line 62 into the bicarbonated water flowing from bicarbonate cartridge 72 to form an electrolytically and physiologically compatible dialysis fluid solution. The pumps and temperature-compensated conductivity sensors used to mix the purified water properly with the bicarbonate and acid are not illustrated but are disclosed in detail in the publications incorporated by reference above.

FIG. 1 also illustrates that dialysis fluid is pumped along a fresh dialysis fluid line 76, through a heater 78 and an ultrafilter 80, before reaching blood filter 40, after which used dialysis fluid is pumped to drain via drain line 82. Heater 78 heats the dialysis fluid to body temperature or about 37° C. Ultrafilter 80 further cleans and purifies the dialysis fluid before reaching blood filter 40, filtering bugs or contaminants introduced for example via bicarbonate cartridge 72 or acid container 74 from the dialysis fluid.

Dialysis fluid circuit 70 also includes a sample port 84 in the illustrated embodiment. Dialysis fluid circuit 70 will further include a blood leak detector (not illustrated but used to detect if a blood filter 40 fiber is torn) and other components that are not illustrated, such as balance chambers, plural dialysis fluid valves, and a dialysis fluid holding tank, all illustrated and described in detail in the publications incorporated by reference above.

In the illustrated embodiment, hemodialysis system 10 is an online, pass-through system that pumps dialysis fluid through blood filter one time and then pumps the used dialysis fluid to drain. Both blood circuit 20 and dialysis fluid circuit 70 may be hot water disinfected after each treatment, such that blood circuit 20 and dialysis fluid circuit 70 may be reused. In one implementation, blood circuit 20 including blood filter 40 is hot water disinfected and reused daily for about one month, while dialysis fluid circuit 70 is hot water disinfected and reused for about six months.

In alternative embodiments, for CRRT for example, multiple bags of sterilized dialysis fluid or infusate are ganged together and used one after another. In such a case, the emptied supply bags can serve as drain or spent fluid bags.

The machine 90 of system 10 includes an enclosure as indicated by the dotted line of FIG. 1. The enclosure of machine 90 varies depending upon the type of treatment, whether the treatment is in-center or a home treatment, and whether the dialysis fluid/infusate supply is a batch-type (e.g., bagged) or on-line.

Figure 2:
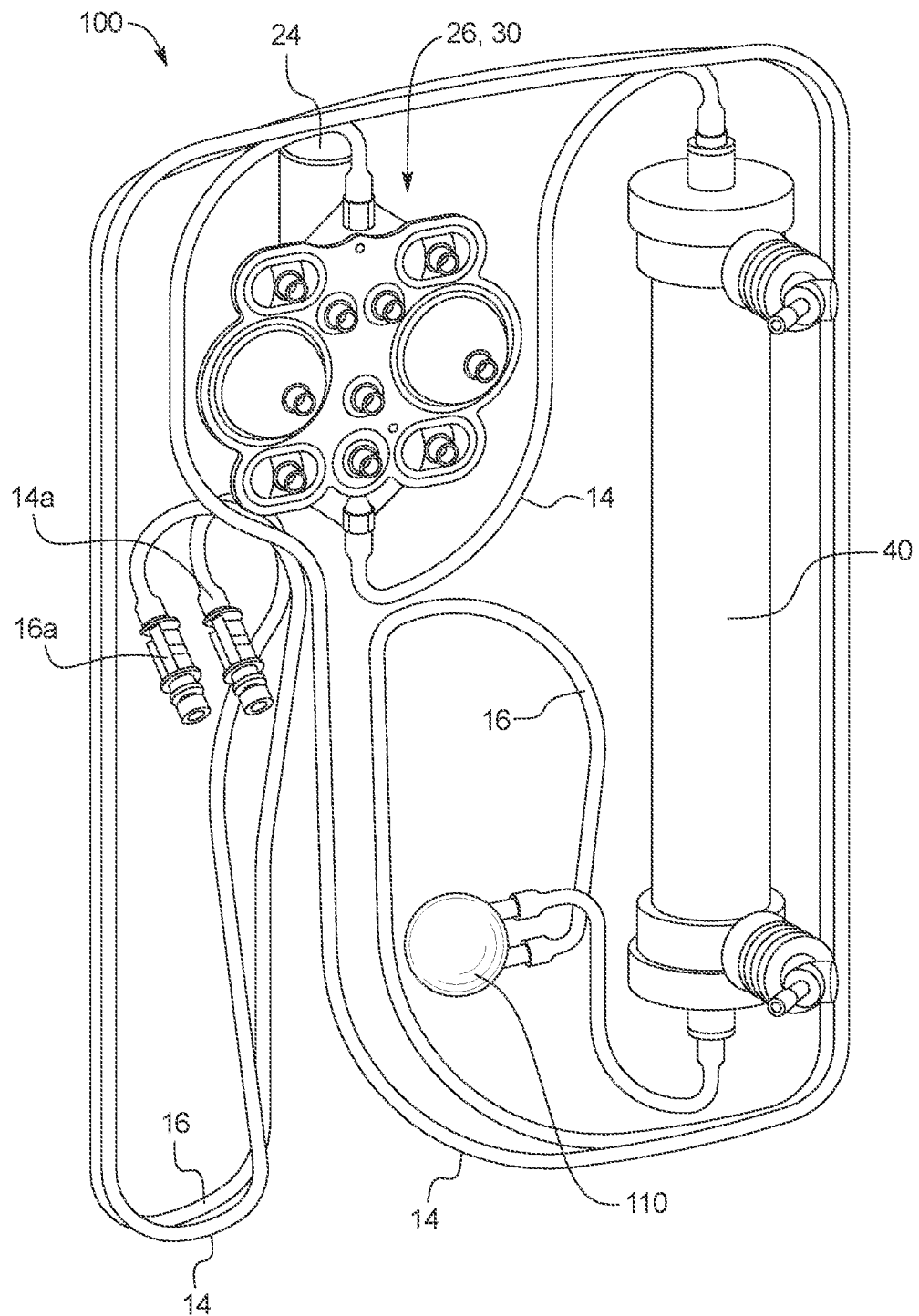
FIG. 2 is a perspective view illustrating a blood set for use with the renal failure therapy machine of FIG. 1.

FIG. 2 illustrates that machine 90 of system 10 of FIG. 1 may operate with a blood set 100. Blood set 100 includes arterial line 14, venous line 16, heparin vial 24, heparin pump 26/blood pump 30 and blood filter 40 (e.g., dialyzer). An airtrap 110 may be located in venous line 16 to remove air from the blood before being returned to patient 12.

Pneumatic Pump Box

In FIGS. 1 and 2, any of pumps 26, 30 (30a and 30b), 64, 96 (and other pumps not illustrated) and any of the valves, such as valves 32i, 32o, 34i, 34o, 68i, 68o, 98i and 98o may be pneumatically actuated. In an embodiment, each of the pumps and valves has a fluid side and an air side, separated by a flexible membrane. Negative pneumatic pressure may be applied to the air side of the membrane to draw fluid into a pump chamber or to open a valve (or pump or valve could be opened by venting positive closing pressure to atmosphere and allowing fluid pressure to open). Positive pneumatic pressure is applied to the air side of the membrane to expel fluid from a pump chamber or to close a valve.

Figure 3:
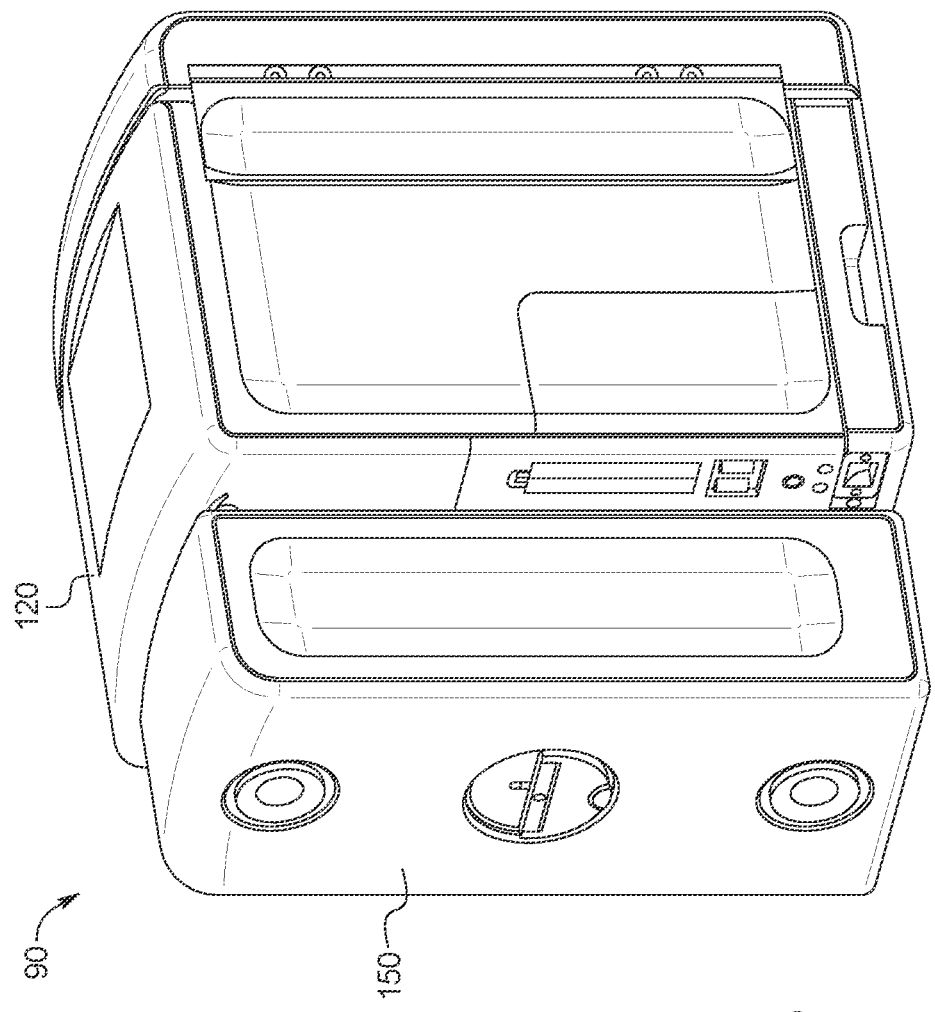
FIG. 3 is a perspective view of one embodiment of the renal failure therapy machine of FIG. 1.

Referring now to FIG. 3, an embodiment of a medical fluid delivery machine 90, such as an HD machine, is illustrated. Medical fluid delivery machine 90 in the illustrated embodiment includes a medical fluid delivery chassis 120 connected to a pneumatic pump box 150. In an embodiment, pneumatic pump box 150 is connected removeably to medical fluid delivery chassis 120, so that the pump box can be moved away from the patient (e.g., placed in a closet) to reduce noise in the treatment area near the vicinity of the patient. At least one positive pneumatic line and at least one negative pneumatic line (not illustrated) run from pneumatic pump box 150 to medical fluid delivery chassis 120 to drive pumps 26, 30 (30a and 30b), 64, 96 (and other pumps not illustrated) and any of the valves, such as valves 32i, 32o, 34i, 34o, 68i, 68o, 98i and 98o, which are located within or are mounted onto medical fluid delivery chassis 120.

In an embodiment, pneumatic components, such as, pneumatic regulators, electrically actuated binary solenoid valves, and electrically actuated variable pneumatic (varivalves) are located within medical fluid delivery chassis 120. The number of pneumatic lines running from pneumatic pump box 150 to medical fluid delivery chassis 120 can therefore be minimized, perhaps to a single positive pressure pneumatic line and a single negative pressure pneumatic line.

Figure 4A:
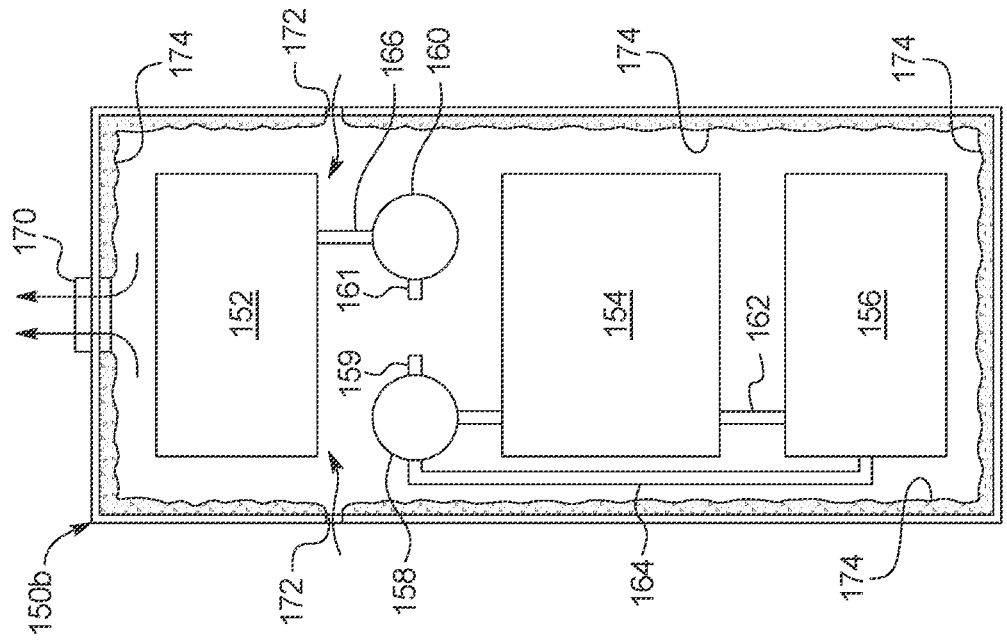
FIG. 4A is a cross-sectional elevation view of one embodiment of a pneumatic pump box of the present disclosure.
Figure 4B:
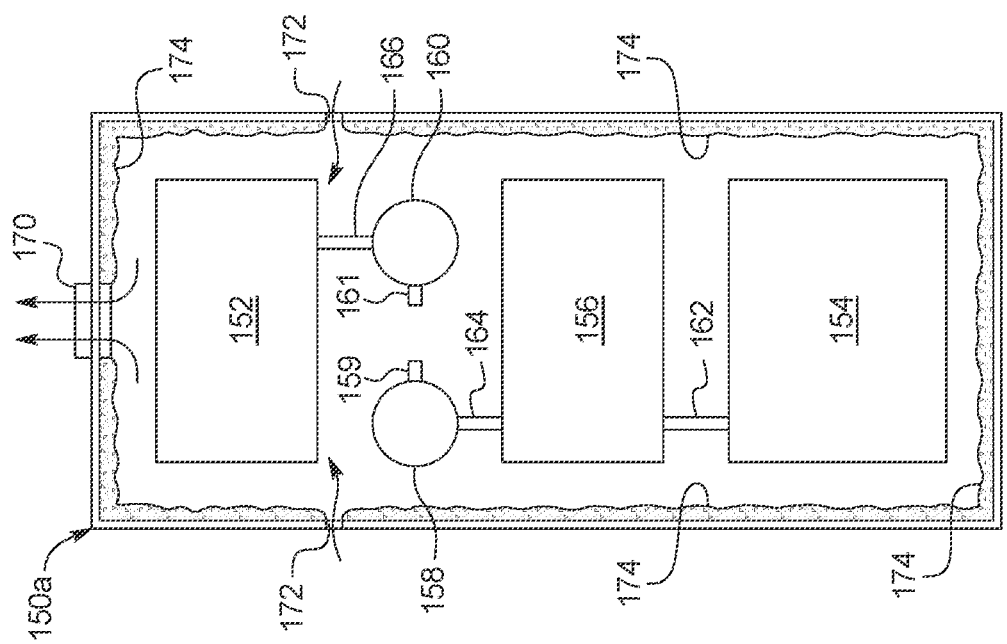
FIG. 4B is a cross-sectional elevation view of a second embodiment of a pneumatic pump box of the present disclosure.

FIGS. 4A and 4B illustrate alternative pneumatic pump boxes 150a and 150b (collectively pump box 150) in more detail. Pump boxes 150a and 150b have been simplified to highlight their primary components and may contain other structure, not illustrated, such as electrical wiring and circuitry, tubing, connectors, etc. Pneumatic pump boxes 150a and 150b of FIGS. 4A and 4B, respectively, recognize that the vacuum pump 152 produces heat and accordingly forms the hottest point in the pump box during operation. Vacuum pump 152 is accordingly mounted at the top within both pneumatic pump boxes 150a and 150b, so that heat may rise up and away from the other pump box components.

Pneumatic pump box 150a also reduces and simplifies the routing of tubing within the pneumatic pump box as much as possible. To do so, pneumatic pump box 150a locates a compressor 154 at the bottom of pneumatic pump box 150a. Compressor 154 feeds compressed air into a dryer 156 via a short pneumatic line 162. Dryer 156 in an embodiment cools the compressed air from compressor 154, condensing water out of compressed air. Removing water from the air prior to use is important because water in the compressed air volume can cause system failure due to corrosion. Because dryer 156 operates in an embodiment via cooling, it is prudent to locate dryer 156 away from the heat-producing vacuum pump 152. In pump box 150a, dryer 156 is located beneath vacuum pump 152, avoiding its rising heat, and is separated from vacuum pump 152 via accumulators 158 and 160. Tubing routing is likewise simplified and reduced via short pneumatic line 164 between dryer 156 and positive pressure accumulator 158 and short tubing line 166 between vacuum pump 152 and negative pressure accumulator 160.

Positive pressure accumulator 158 includes an output port 159 for connecting to a positive pressure pneumatic line (not illustrated), supplying positive pressure to medical fluid delivery chassis 120. Negative pressure accumulator 160 includes an output port 161 for connecting to a negative pressure pneumatic line (not illustrated), supplying negative pressure to medical fluid delivery chassis 120.

Alternative pneumatic pump box 150b flips the placement of compressor 154 and dryer 156 relative to pneumatic pump box 150a, so that compressor 154 instead lies above dryer 156. This configuration moves cooling dryer 156 further away from heat-producing vacuum pump 152 and also below heat rising from the compressor, which is advantageous, but requires a longer pneumatic line 164 between dryer 156 and positive pressure accumulator 158. In any case, component layouts of both pneumatic pump box 150a and 150b are made with efficiency and simplicity in mind.

Either one or both of pneumatic pump boxes 150a and 150b may provide an electrically operated fan 170 at the top of the box, which is oriented to pull heated air from vacuum pump 152 out of the box. To aid in the circulation of cooler ambient air about vacuum pump 152, inlet vents 172 may be provided and located as illustrated just beneath the location of vacuum pump 152. As illustrated by the convection arrows in FIGS. 4A and 4B, relatively cool air is pulled in through vents 172 and about vacuum pump 152 via fan 172, which also exhausts the heated out of pneumatic pump box 150a or 150b.

Either one or both of pneumatic pump boxes 150a and 150b may also provide sound insulation 174 on one or more or all of the inner walls of the pump boxes. Sound insulation 174, such as foam or rockwool, lining the inner walls of pump boxes 150a and 150b, helps to muffle noise produced via pneumatic components 152, 154 and 156. The insulation may eliminate the need to remove pump box 150 from medical fluid delivery chassis 120. Indeed, it is contemplated to integrate pump box 150, including any of the disclosure and alternatives described herein, into medical fluid delivery chassis 120 of machine 90.

Figure 5:
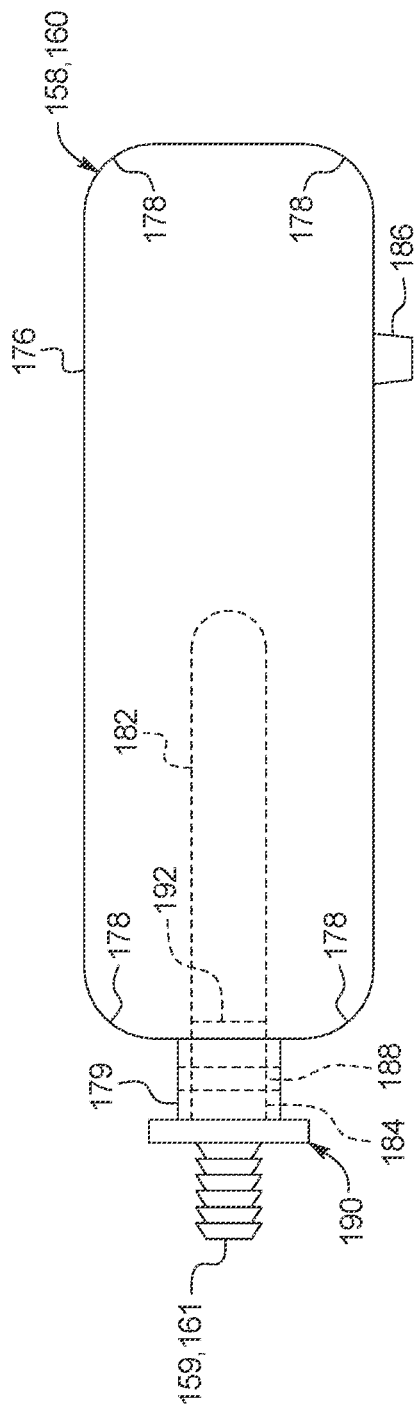
FIG. 5 is a side elevation view of one embodiment of a pneumatic pressure accumulator of the present disclosure.
Figure 6:
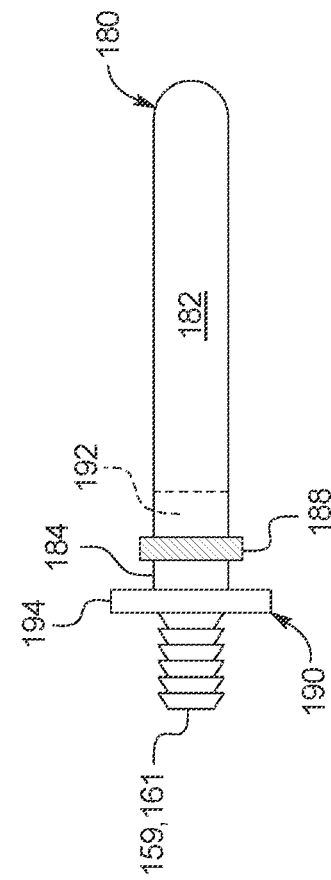
FIG. 6 is a side elevation view of a bladder assembly used with the pneumatic pressure accumulator of the present disclosure.
Figure 7:
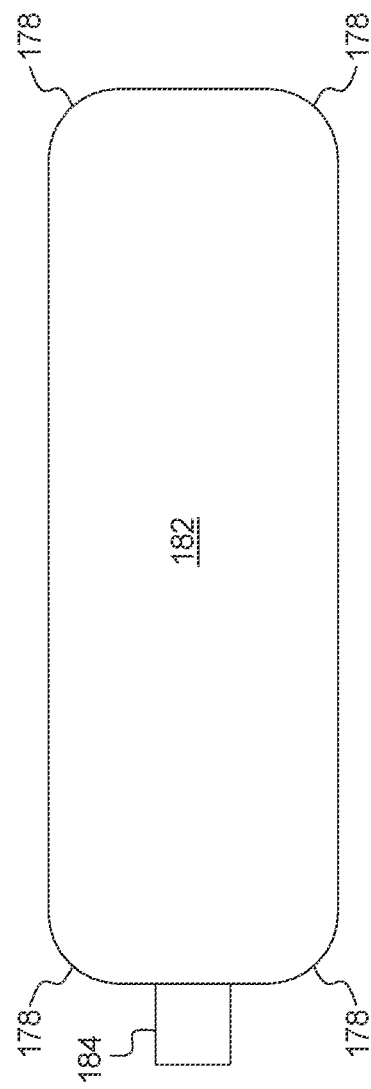
FIG. 7 is a side elevation view of a bladder, which can be either a bladder inflated under positive pressure within the positive pressure accumulator or a bladder inflated under negative pressure within the negative pressure accumulator.

Referring now to FIGS. 5 to 7, embodiments of pressure accumulators 158, 160 are illustrated. As illustrated in FIG. 5, positive pressure accumulator 158 includes a rigid outer housing 176, which can be made of a plastic material, such as polyvinylchloride ("PVC"), polycarbonate ("PC"), polypropylene ("PP"), polyethylene ("PE"), for example. Rigid outer housing 176 in the illustrated embodiment has an inner surface that attempts two eliminate sharp corners and instead includes relatively large radius bends 178 that enable a bladder to conform readily to a shape of the inner surface, to use all or substantially all of the inner volume defined by the inner surface. In an embodiment, the inner volume defined by rigid housing may be from about 250 milliliters to a liter or more, e.g., 500 milliliters.

Rigid outer housing 176 in the illustrated embodiment includes or provides a vent port 186. Vent port 186 is in one embodiment molded with the rest of rigid housing 176. Vent port 186 allows a bladder 182 described below to push air out of housing 176 when bladder 182 expands and for air to enter housing 176 when bladder 182 contracts. Housing 176 nevertheless provides the ridged enclosure needed to contain the bladder 182. Port 186 helps the bladder to expand fully and contract readily.

An open end of rigid outer housing 176 in the illustrated embodiment accepts a bladder assembly 180 illustrated in FIG. 6. Bladder assembly 180 includes an expandable bladder 182. Expandable bladder 182 is made of a highly elastic material, such as latex. FIG. 6 illustrates that the open end 184 of bladder 182 is stretched and sealed over a bladder connection end 192 of a connector 190. Connector 190 also provides output ports 159, 161 described above in connection with FIGS. 4A and 4B, respectively, for connecting to positive or negative pressure lines (not illustrated), supplying positive or negative pressure to medical fluid delivery chassis 120. Output ports 159, 161 may be barbed as illustrated for sealed connection with the pneumatic lines, or have other suitable airtight sealing connections. Connector 190 may be made from any of the rigid plastics described above for rigid outer housing 176, including nylon additionally. Connector 190 may also be injection molded to provide closer tolerances than can be achieved via blow molding, which may be used to form rigid housing 176.

A gasket 188, such as an o-ring gasket further compresses expandable bladder 182 onto bladder connection end 192 of a connector 190. Bladder connection end 192 in an embodiment provides an annular indent to seat gasket 188 onto bladder 182 and bladder connection end. Gasket 188 is also sized to compresses within a neck 179 of rigid outer housing 176 when bladder assembly 180 is inserted into outer housing 176. A flange 194 of connector 190 seats against the front of neck 179 when bladder assembly 180 is fully inserted into outer housing 176. Gasket 188 may be made of silicon or other compressible rubber or plastic.

In an alternative embodiment, both output ports 159, 161 and bladder connection end 192 of connector 190 are barbed. Housing 176 and its neck 179 may be made of a softer material than barbed connection end 192 of connector 190, such that the barbs can dig into and seal to neck 179 of housing 176.

In a further alternative embodiment, output ports 159, 161 of connector 190 may be smooth and seal to a pneumatic tube via one or more o-ring gasket, e.g., fitted into groove formed in output ports 159, 161. Here, bladder connection end 192 can be smooth as illustrated or barbed as described alternatively above.

Assume for purposes of illustration that a positive pressure regulator, such as a static regulator or a vari-valve, sets the operating pressure at the fluid pump chamber or fluid valve chamber to 5 psig. It is contemplated then to construct bladder 182 (e.g., via setting its wall thickness), so that it requires at least slightly above 5 psig, such as 5.5 psig, to inflate the bladder. The pressure needed to inflate the bladder also needs to be below the output pressure of compressor 154 and dryer 156. By doing so, bladder 182 provides sufficient operating pressure to the regulator when the bladder contracts from its expanded shape illustrated in FIG. 7 to its resting shape illustrated in FIGS. 5 and 6. Without bladder 182, once the pressure in rigid outer housing 176 falls to 5 psig in the example, accumulator 158 can no longer power a fluid valve or pump. But with bladder 182, once the pressure in rigid outer housing 176 falls to the bladder inflation pressure (e.g., slightly above 5 psig or 5.5 psig in the example), bladder 182 supplies the bladder inflation pressure to the regulator, e.g., 5.5 psig, until bladder 182 reaches its resting shape.

Figure 8A:
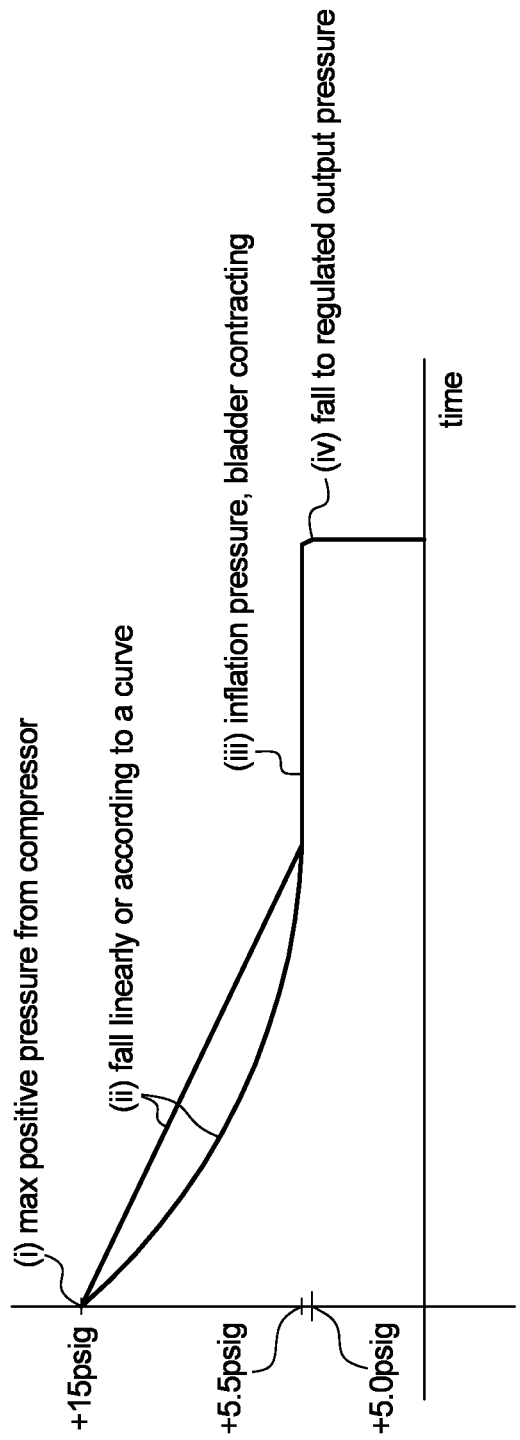
FIG. 8A is one example graph of the pressure provided by positive pressure accumulator over time.

FIG. 8A illustrates a graph of the pressure provided by accumulator 158 over time, showing the pressure (i) start at the initial positive pressure provided by compressor 154 to accumulator 158, (ii) fall either linearly or according to a curve to the bladder inflation pressure, (iii) remain at the inflation pressure until bladder 182 reaches its non-expanded resting shape, and (iv) fall to the regulated output pressure.

The additional amount or volume may be used, for example, to drive a pump or valve chamber when power to compressor 154 is no longer available. The additional amount or volume may also be used to lessen the leak-tightness requirements for the pneumatic components, such as the regulators, binary solenoid valves and vari-valves. Lessening such requirements may allow of a cheaper valve to be used and/or lessen the number of fault situations when such pneumatic components are tested before treatment.

FIGS. 5 to 7 also illustrate an embodiment of negative pressure accumulator 160. All of the above structure and alternatives described above for positive pressure accumulator 158 are the same for negative pressure accumulator 160, except that (i) bladder 182, e.g., made of latex, silicone or other flexible material, is thickened to have a higher inflation pressure and (ii) the roles of vent port 186 and connector 190 are reversed, so that vent port becomes the vacuum source port and connector 190 becomes the air vent. With negative pressure accumulator 160, vacuum pump 152 draws a vacuum on port 186, which evacuates the air between bladder 182 and rigid outer housing 176, while air is able to enter the inside of bladder 182 via connector 190 to backfill the bladder.

Negative pressure bladder 182 is structured (e.g., via setting its wall thickness), such that it takes a full vacuum amount of negative pressure to inflate the bladder in one embodiment. For example, if it is desired to charge negative pressure accumulator 160 to −15 psig, negative pressure bladder 182 may be structured such that it takes −15 psig to inflate the bladder, assuming vacuum pump 152 can provide at least −15 psig. In this manner, the space between fully contracted bladder 182 and rigid outer housing 176 is fully evacuated to a full, desired amount prior to bladder inflating to cover vacuum inlet port 186. In various embodiments, (i) the bladder and the ridged outer housing accumulator are configured so that a full vacuum can be drawn before the negative pressure bladder expands to block or fully block the vacuum port provided by the housing, and/or (ii) the vacuum port can be angled on the inside of the rigid housing so that it is difficult for the bladder to block. When in use, once the negative pressure begins to fall below the negative pressure inflation level, bladder 182 begins to contract, supplying the negative inflation pressure until the bladder is contracted fully. When bladder 182 is fully contracted, rigid outer housing 176 is left with a fully charged vacuum.

Figure 8B:
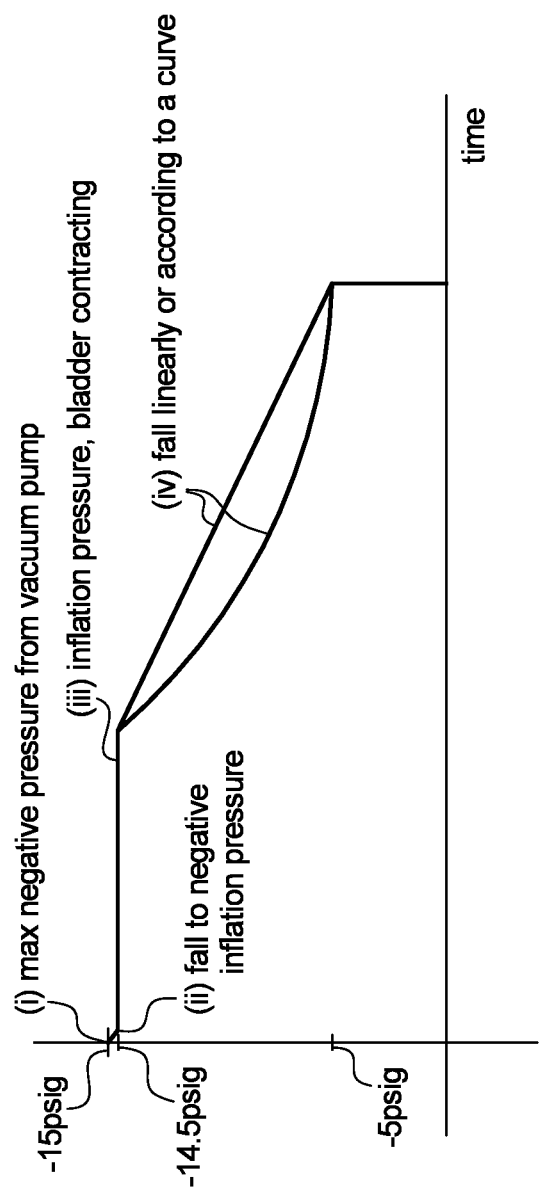
FIG. 8B is one example graph of the negative pressure provided by negative pressure accumulator over time.

FIG. 8B illustrates a graph of the negative pressure provided by accumulator 160 over time, showing the pressure (i) start at the initial negative pressure setpoint provided by vacuum pump 152 to accumulator 160, (ii) fall slightly to or just below the negative inflation pressure of bladder 182, (iii) remain at the negative inflation pressure until bladder 182 is fully contracted, and (iv) fall either linearly or according to a curve to a negative regulated output pressure. Vent 190 allows air to escape the inside of bladder 182 so that the bladder may contract fully.

One illustrative pressure setting example for positive pressure accumulator 158 versus negative pressure accumulator 160 is as follows: (pos) positive pressure chamber pressure +15 psig, positive pressure bladder inflation pressure +5.5 psig, positive pressure regulated output pressure +5.0 psig, versus (neg) negative pressure chamber pressure −15 psig, negative pressure bladder inflation pressure −14.5 psig, negative pressure regulated output pressure −5.0 psig.

Figure 9:
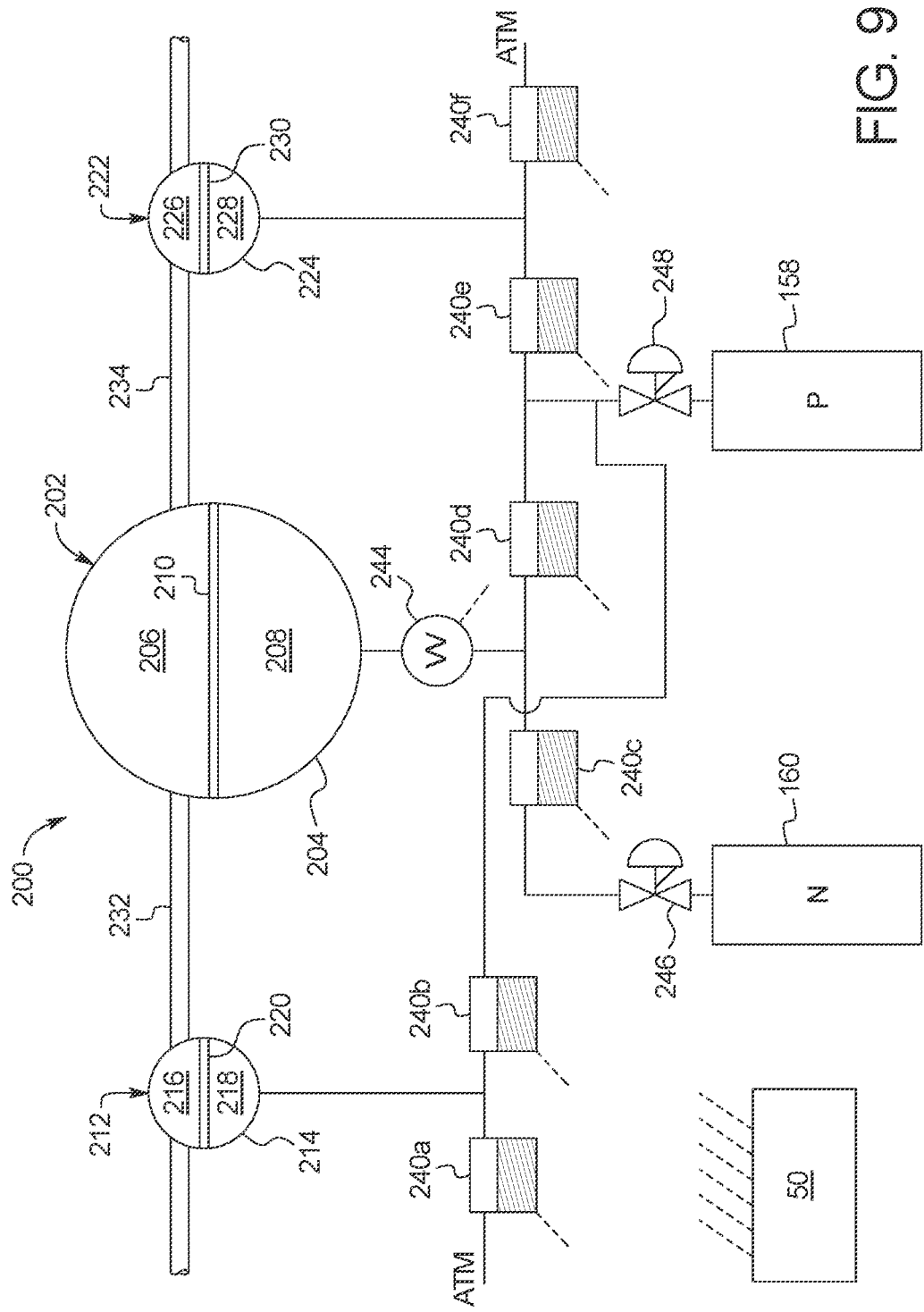
FIG. 9 is a flow schematic of one embodiment of the accumulators of the present disclosure operating with a medical fluid pump including a pneumatically actuated pump chamber and first and second pneumatically actuated medical fluid valve chambers located respectively upstream and downstream of the pneumatically actuated pump chamber.

Referring now to FIG. 9, for use in power loss situations, battery power may be provided with accumulators 158 and 160 and associated bladders 182 to power the electrically operated solenoid and vari-valves, so that negative and positive pressure may be applied to a medical fluid pump 200 including a pneumatically actuated pump chamber 202 and first and second pneumatically actuated medical fluid valve chambers 212 and 222 located respectively upstream and downstream of the pneumatically actuated pump chamber 202. Binary solenoid valves 240a to 240f are in one embodiment spring closed and powered open, so that batter power is only needed to open the valves. Vari-valve 244 needs power throughout its operation. Static pneumatic regulators 246 and 248 in one embodiment do not need power. Static pneumatic regulators 246 and 248 set constant positive and negative pneumatic operating pressures as discussed above.

Viewing additionally the blood set 100 of FIG. 2, to rinse blood back to the patient towards connectors 14a and 16a through the blood set using dialysis fluid across dialyzer 40 to push the blood, battery power is needed to open the solenoids and operate the vari-valves associated with the blood pump (which may be configured like pump 200) and/or a fresh dialysis fluid pump (which may be configured like pump 200). Balance chambers may also be employed, which are bypassed for rinseback in one embodiment. The used dialysis fluid pump may be shut down (inlet and outlet valves closed), so that positive dialysis fluid pressure may be built in the dialyzer for the dialysis fluid flow into the blood set to push blood back towards the patient.

FIG. 9 illustrates that in one embodiment, pneumatically actuated pump chamber 202 includes a housing 204, e.g., a rigid plastic housing, defining a medical fluid side 206 (e.g., blood, dialysis fluid, substitution fluid, intravenous drug) and a pneumatic side 208, separated by a flexible membrane or diaphragm 210. Pneumatically actuated first or inlet valve 212 includes a housing 214, e.g., a rigid plastic housing, defining a medical fluid side 216 and a pneumatic side 218, separated by a flexible membrane or diaphragm 220. Pneumatically actuated second or outlet valve 222 includes a housing 224, e.g., a rigid plastic housing, defining a medical fluid side 226 and a pneumatic side 228, separated by a flexible membrane or diaphragm 230. Inlet valve 212 selectively allows medical fluid to flow to pump chamber 202 via medical fluid inlet line 232, while outlet valve 222 selectively allows medical fluid to flow from pump chamber 202 via medical fluid outlet line 234.

To draw medical fluid into pump chamber 202, inlet valve 212 is opened, outlet valve 222 is closed and negative pneumatic pressure is applied to pumping membrane 210 to pull the membrane towards vari-valve 244, sucking fluid into pump chamber 202 via inlet line 232. To push medical fluid from pump chamber 202, inlet valve 212 is closed, outlet valve 222 is opened and positive pneumatic pressure is applied to pumping membrane 210 to push the membrane away from vari-valve 244, pushing fluid from pump chamber 202 via outlet line 234. Vari-valve 244 includes a variable orifice that allows a desired variation of positive and/or negative pneumatic pressure, within ranges set by pneumatic regulators 246 and 248, over the course of a stroke of pump chamber 202. Binary valve 240c (e.g., spring closed, energized open) selectively allows regulated negative pressure to reach vari-valve 244, while binary valve 240d (e.g., spring closed, energized open) selectively allows regulated positive pressure to reach vari-valve 244.

In the illustrated embodiment, first or inlet valve 212 and second or outlet valve 222 are closed under positive pressure and opened to atmosphere. To close inlet valve 212, binary valve 240b is opened, while binary valve 240a is closed, allowing regulated positive pressure to close inlet valve 212 and to prevent the positive pressure from venting to atmosphere. To open inlet valve 212, binary valve 240b is closed, while binary valve 240a is opened, preventing regulated positive pressure from reaching inlet valve 212 and enabling the existing positive pressure at inlet valve 212 to vent to atmosphere. Likewise, to close outlet valve 222, binary valve 240e is opened, while binary valve 240f is closed, allowing regulated positive pressure to close outlet valve 222 and to prevent the positive pressure from venting to atmosphere. To open outlet valve 222, binary valve 240e is closed, while binary valve 240f is opened, preventing regulated positive pressure from reaching outlet valve 222 and enabling the existing positive pressure at outlet valve 222 to vent to atmosphere.

Binary valves 240a to 240f and vari-valve 244 (as indicated by dashed electrical lines) are operated under the control of control unit 50 (also showing dashed electrical lines). Control unit 50 runs a computer program that sequences binary valves 240a to 240f as discussed above and controls the orifice size of vari-valve 244 to create a desired pumping pressure profile.

Inlet and outlet valves 212 and 222 may open when vented to atmosphere via medical fluid pressure, forcing valve membranes 220 and 230 open, and/or by forming valve membranes 220 and 230 to be preformed or predomed into a sphere or dome and orienting the dome towards the pneumatic inlet, such that the natural bias of the membrane itself causes or tends to cause the inlet and outlet valves 212 and 222 to open when not subjected to positive pneumatic pressure.

In the illustrated embodiment, inlet and outlet valves 212 and 222 do not require negative pressure, and more positive pressure is therefore needed to operate medical fluid pump 200 than negative pressure. Thus even if bladder 182 is only provided with positive pressure accumulator 158, the life of medical fluid pump 200 is still extended upon power loss. In an alternative embodiment, negative pressure is used to open inlet and outlet valves 212 and 222, and thus a roughly equal amount positive and negative pressure is needed to operate medical fluid pump 200. Here, bladder 182 may be provided with both positive and negative pressure accumulators 158 and 160 to extend the life of medical fluid pump 200 upon power loss.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid delivery machine comprising:
a medical fluid pump including a pneumatically actuated pump chamber and first and second pneumatically actuated medical fluid valve chambers located respectively upstream and downstream of the pneumatically actuated pump chamber;
a pneumatic regulator for regulating positive pressure air; and
an accumulator storing the positive pressure air for delivery to a destination having an operating pressure set by the pneumatic regulator, the destination including at least one of the pneumatically actuated pump chamber, the first pneumatically actuated medical fluid valve chamber, or the second pneumatically actuated medical fluid valve chamber, the accumulator holding an elastic bladder constructed with a wall thickness that is selected based on the set operating pressure and a pressure of the positive pressure air supplied to the accumulator for storage, wherein the elastic bladder inflates from a resting shape at a bladder inflation pressure, which is a positive pressure greater than the operating pressure set by the pneumatic regulator and less than the pressure of the positive pressure air supplied to the accumulator for storage, thereby creating additional positive pressure such that when the pressure in the bladder falls to the bladder inflation pressure from an initial pressure greater than the bladder inflation pressure, the bladder supplies the bladder inflation pressure until the bladder reaches its resting shape, wherein the accumulator includes an outer rigid housing holding the elastic bladder, wherein the bladder is held in a sealed relationship with the outer rigid housing, and wherein the outer rigid housing includes a vent port that is configured to enable air to escape the outer rigid housing as the bladder inflates.

2. The medical fluid delivery machine of claim 1, which includes a connector forming the sealed relationship between the bladder and the outer rigid housing.

3. The medical fluid delivery machine of claim 2, wherein the connector includes a sealing end configured to seal to an open end of the bladder and a tube connecting end configured to seal to a pneumatic tube extending from the accumulator.

4. The medical fluid delivery machine of claim 1, wherein the outer rigid housing is contoured to enable the elastic bladder when inflated to conform at least substantially completely to an inner shape of the outer rigid housing.

5. The medical fluid delivery machine of claim 1, wherein the bladder initially has a thin tube shape and inflates to conform at least substantially completely to an inner shape of the outer rigid housing.

6. The medical fluid delivery machine of claim 1, wherein the pneumatic regulator sets the operating pressure for the positive pressure air, the bladder enabling the additional amount of the positive pressure air to be provided to the pneumatic regulator.

7. The medical fluid delivery machine of claim 1, wherein at least one of the first and second pneumatically actuated medical fluid valve chambers is closed via positive pressure and opened via venting to atmosphere.

8. A medical fluid delivery machine comprising:
a medical fluid pump including a pneumatically actuated pump chamber and first and second pneumatically actuated medical fluid valve chambers located respectively upstream and downstream of the pneumatically actuated pump chamber;
a compressor for creating positive pressure air; and
an accumulator storing the positive pressure air for delivery to a destination having an operating pressure set by a pneumatic regulator external to the accumulator, the destination including at least one of the pneumatically actuated pump chamber, the first pneumatically actuated medical fluid valve chamber, or the second pneumatically actuated medical fluid valve chamber, the accumulator holding an elastic bladder constructed with a wall thickness that is selected based on the externally set operating pressure and an output pressure of the compressor, wherein the elastic bladder inflates from a resting shape at a bladder inflation pressure, which is a positive pressure greater than the externally set operating pressure and less than the output pressure of the compressor, thereby creating additional positive pressure such that when the pressure in the bladder falls to the bladder inflation pressure from an initial pressure greater than the bladder inflation pressure, the bladder supplies the bladder inflation pressure until the bladder reaches its resting shape, wherein the accumulator includes an outer rigid housing holding the elastic bladder, wherein the bladder is held in a sealed relationship with the outer rigid housing, and wherein the outer rigid housing includes a vent port that is configured to enable air to escape the outer rigid housing as the bladder inflates.

9. The medical fluid delivery machine of claim 1, which includes a connector forming the sealed relationship between the bladder and the outer rigid housing.

10. The medical fluid delivery machine of claim 9, wherein the connector includes a sealing end configured to seal to an open end of the bladder and a tube connecting end configured to seal to a pneumatic tube extending from the accumulator.

11. The medical fluid delivery machine of claim 1, wherein the outer rigid housing is contoured to enable the elastic bladder when inflated to conform at least substantially completely to an inner shape of the outer rigid housing.

12. The medical fluid delivery machine of claim 1, wherein the bladder initially has a thin tube shape and inflates to conform at least substantially completely to an inner shape of the outer rigid housing.

13. The medical fluid delivery machine of claim 1, wherein the pneumatic regulator is located between the accumulator and the destination, the pneumatic regulator setting the operating pressure for the positive pressure air, the bladder enabling the additional amount of the positive pressure air to be provided to the pneumatic regulator.

14. The medical fluid delivery machine of claim 1, wherein at least one of the first and second pneumatically actuated medical fluid valve chambers is closed via positive pressure and opened via venting to atmosphere.

15. The medical fluid delivery machine of claim 1, further comprising a vacuum pump for creating negative pressure and a second accumulator storing the negative pressure for operation within the medical fluid delivery machine, the second accumulator holding a second elastic bladder that inflates under negative pressure from the vacuum pump applied to an outside of the bladder, increasing the amount of negative pressure that the second accumulator can provide.

16. The medical fluid delivery machine of claim 1, wherein the compressor and the accumulator are provided at a location of the medical fluid delivery machine, the location further including a vacuum pump for supplying negative pneumatic pressure for the medical fluid pump and a dryer for removing water from the positive pressure air outputted from the compressor prior to storage in the accumulator, wherein the compressor and the dryer are located beneath the accumulator and the accumulator is located beneath the vacuum pump.

* * * * *